United States Patent
Redha et al.

(10) Patent No.: US 7,955,342 B2
(45) Date of Patent: Jun. 7, 2011

(54) DEVICE FOR CONNECTING HOLLOW ORGANS, ESPECIALLY BLOOD VESSELS, BY SURGERY

(75) Inventors: Falah Redha, Riyadh (SA); Stefan Kobler, Neuendorf/So (CH); Werner Zumbrunn, Muttenz (CH); Essam Abdulaziz Alshail, Ridyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 476 days.

(21) Appl. No.: 11/997,387

(22) PCT Filed: Aug. 2, 2006

(86) PCT No.: PCT/CH2006/000399
§ 371 (c)(1),
(2), (4) Date: Dec. 16, 2008

(87) PCT Pub. No.: WO2007/014482
PCT Pub. Date: Feb. 8, 2007

(65) Prior Publication Data
US 2009/0131957 A1 May 21, 2009

(30) Foreign Application Priority Data
Aug. 3, 2005 (CH) ...................... 1286/05

(51) Int. Cl.
*A61B 17/08* (2006.01)
(52) U.S. Cl. ...................................... 606/153
(58) Field of Classification Search .................. 606/153, 606/213, 215, 216
See application file for complete search history.

(56) References Cited

U.S. PATENT DOCUMENTS

| | | | |
|---|---|---|---|
| 3,040,748 A | 6/1962 | Klein et al. | |
| 4,214,586 A | 7/1980 | Mericle | |
| 4,470,415 A | 9/1984 | Wozniak | |
| 4,624,255 A | 11/1986 | Schenck et al. | |
| 2005/0182430 A1 | 8/2005 | Schenck | |

FOREIGN PATENT DOCUMENTS
FR 2 422 621 6/1980

OTHER PUBLICATIONS

International Search Report for International Application No. PCT/CH2006/000399, Oct. 6, 2006.

*Primary Examiner* — Julian W Woo
(74) *Attorney, Agent, or Firm* — Pearl Cohen Zedek Latzer, LLP

(57) ABSTRACT

The invention elates to a device (20) for connecting hollow organs (24, 25), which device comprises various elements that are held by holding devices. Said holding devices can be laterally displaced on a slide rail (21), rotated or detached and put on and their position can be secured if required. The traverse (31) is used as a stop for the axial alignment of the holding devices. The two holding devices (22, 23) carry clamping devices for retaining and, if required, clamping off the hollow organ ends (24, 25). The holding devices (26, 27) carry fittings (10, 11). The two hollow organ ends (24, 25) to be connected are pushed through the fittings to such an extent as to project over the fitting ends by a defined extent. The ends of the hollow organs are then turned up by the ends of the fittings using two turn-up devices (28, 29). The holding device (30) in the center holds an additional fitting (14) into which the two fittings (10, 11) are inserted with the turned-up hollow organ ends and secured.

10 Claims, 3 Drawing Sheets

DEVICE FOR CONNECTING HOLLOW ORGANS, ESPECIALLY BLOOD VESSELS, BY SURGERY

CROSS-REFERENCE TO RELATED APPLICATIONS

This application is a National Phase Application under 35 U.S.C. 371 of PCT International Application No. PCT/CH2006/000399, International Filing Date Aug. 2, 2006, claiming priority of Switzerland Patent Application No. 1286/05, filed Aug 3, 2005, which is hereby incorporated by reference in its entirety.

FIELD OF THE INVENTION

The invention relates to a device for the anastomosis of hollow organs.

BACKGROUND OF THE INVENTION

One important task in surgery is end-to-end anastomosis. In the text which follows, this should be understood to mean in particular the surgical connection of blood vessels. However, the techniques described below can in principle also be used for the anastomosis of any hollow organ ends.

In end-to-end anastomosis, stitching is the most frequently used connection technique. However, instead of stitching, which takes a lot of time, the connection can also be achieved in a fraction of the time by using fittings or sleeves. For this purpose, a sleeve which is preferably biodegradable is pushed over each of the two vessel ends. The inner diameter of said sleeve must correspond approximately to the outer diameter of the vessels. The sleeve is in each case pushed over the vessel until the end of the vessel protrudes slightly out of the sleeve. The end of the vessel then has to be turned over around the end of the sleeve so that the sleeve is secured and the inner side of the vessel, the tunica intima, is facing outwards. The two sleeves are then pushed into a third fitting and are fixed in the latter in such a way that the inner sides of the two vessels make contact with one another around the entire circumference. This is necessary in order for the two vessel ends to be able to grow together.

During this procedure, the work of the surgeon can be facilitated by various auxiliary means, for example by using devices which hold and clamp the ends of the blood vessels, which hold fittings and help to align these with one another in the axial direction, which make it easier to push the fittings together, or by using a device which assists and facilitates the process of turning the ends of the blood vessels over around the ends of the fittings.

Many auxiliary means for the anastomosis of vessels have already been known for decades. U.S. Pat. Nos. 4,474,181 and 4,624,255 disclose a device which consists essentially of a ring having a diameter larger than the outer diameter of the blood vessel. The vessel ends to be connected are firstly stitched together at least at three points. The ring is then pushed over the stitching area. Using the threads of the stitches, the vessel is widened to the diameter of the ring and is fixed to the ring in this position. As a result, the inner sides of the two vessels are brought into contact with one another. U.S. Pat. Nos. 4,016,883 and 4,165,747 contain examples of clamps, especially for blood vessels having a small diameter. U.S. Pat. No. 4,165,747 moreover proposes clamps which are arranged in a displaceable manner on a common rail. In this way, the blood vessels can be simultaneously clamped and can be fixed in position relative to one another; this makes it easier to stitch them together.

Further devices which ensure the mutual axial alignment of the vessel ends and fittings are described in U.S. Pat. Nos. 1,151,300, 2,940,451 and 3,048,177. In all cases, at least one vessel end must be turned over around a sleeve prior to the connection operation so that the inner sides of the two vessels make contact with one another after being joined.

Unlike the abovementioned patent specifications, U.S. Pat. No. 2,453,056 describes how the turning-over of the vessel ends is achieved, namely by using tweezers. It is known that it is very difficult to turn vessels over using a number of pairs of tweezers, and this process sometimes requires more than one person. Even if the surgeon is assisted by a mechanical device which is able to hold and guide a number of pairs of tweezers or grippers in a suitable manner, there is still the risk that the vessel ends will be damaged during the manipulations.

U.S. Pat. No. 2,453,056 demonstrates that the use of sleeves or fittings as auxiliary means for anastomosis has already been known for a very long time. Patents U.S. Pat. Nos. 3,221,746, 3,254,650, 3,254,651, 3,774,615, 4,366,819 or 2004/0199189 A1 also propose the use of fittings.

Various auxiliary means have also been developed for turning the vessel ends over around the end of a sleeve. GB 1413191 proposes a number of spikes which are formed on the outside of the sleeve and can be moved in the axial direction. They have barbs pointing outwards and protrude slightly beyond the end of the sleeve. The edge of the vessel, which has previously been pushed through the sleeve, is pulled and respectively pushed onto the barbs by means of tweezers.

The spikes are then retracted. The vessel end is thus pulled over the end of the sleeve.

U.S. Pat. No. 2,940,452 proposes the use of an elastomer membrane. The latter is pulled taut over the end of a tube. A cylindrical piston with a conical end is then pushed forward through the interior of the tube until the membrane has a conical bulge. In this position, the piston with the membrane pulled taut over it is pushed into the end of the blood vessel protruding beyond a sleeve and then is pressed against the sleeve. The outer tube is then pushed in the direction of the vessel. In the process, the membrane is placed around the end of the sleeve, and with it the protruding part of the blood vessel.

U.S. Pat. No. 3,180,337 describes a similar device, but without the membrane. A cylindrical piston with a conical end is again used. The cylindrical part of the piston is surrounded by an axially displaceable tubular part made of elastic material. Firstly, the conical end of the piston is pushed into the end of the blood vessel protruding beyond a sleeve and then is pressed against the sleeve. The aforementioned tubular piece is then pushed over the piston in the direction of the blood vessel. The tubular piece firstly upsets the protruding end of the blood vessel, then widens together with the end of the blood vessel, and finally both are turned over around the end of the sleeve.

U.S. Pat. No. 2,779,996 describes an elastic ring as an auxiliary means, which is pushed into the interior of the protruding part of the vessel end. After being inserted, the ring—and thus also the protruding part of the vessel—is widened by means of compressed air, and in this way the protruding part of the vessel end is turned over around the sleeve.

The device according to U.S. Pat. No. 3,040,748 is similar to the auxiliary devices in U.S. Pat. Nos. 2,940,452 and 3,180,337. It uses a cylindrical piston with a conical end in a known manner. A thin tubular piece made of an elastic material is pulled on behind the conical head. The rear end of this tube has a bead. It is held by a further tube which can be displaced in the axial direction, and is already widened. In a known manner, the piston with the conical end is pushed into the protruding part of the blood vessel and then pressed against the sleeve. This operation is assisted by a fluid which is pumped through the tip of the conical piston head into the clamped vessel. The fluid flows between the vessel and the piston and also through the tubular piece made of elastic material, and thus makes it easier to push the vessel end onto the tubular piece. Once it has been pushed on, the flow of fluid is stopped. The outer, displaceable tube is then pushed in the direction of the sleeve. It takes with it the elastic tubular piece—and thus the vessel end pushed over the latter—and turns both of these over around the sleeve.

U.S. Pat. No. 4,055,186 describes a press-fastening system for joining two parts of an intestine. Attached to both parts of the press fastener is a concentric ring which is mounted in a flexible manner in the axial direction. The rings have an outer diameter which is somewhat smaller than the inner diameter of the intestine parts to be connected. The press-fastener parts with the rings are pushed into the ends of the intestine parts and then the latter are turned over inwards around the rings. There is no description as to how this is to be achieved. The press-fastener parts are then joined and latched together. Thanks to the flexible rings, the two intestine parts are pressed against one another with a defined force.

All the aforementioned devices for the anastomosis of blood vessels have certain drawbacks with regard to handling or their function. The object of the invention is therefore to find an improved device for anastomosis without the drawbacks of the prior art.

SUMMARY OF THE INVENTION

According to the invention, this object is achieved by a device which is characterized by the features specified below.

Firstly, a turning-over device is described which is characterized by a very small space requirement and extremely easy operation. The first preparation step for the turning-over operation corresponds to the conventional procedure: a cylindrical sleeve is pushed over a vessel end until the latter protrudes from the sleeve by a certain extent. The protruding part of the vessel should be long enough that the sleeve is sufficiently secured after the vessel end has been turned over. It is also necessary that the vessel is further clamped at the rear and that its end is cleanly prepared, for example by a cut perpendicular to the longitudinal axis of the vessel.

A rotationally symmetrical auxiliary device is then pushed towards the opening of the vessel from the outside, in axial alignment therewith. The front part of this auxiliary device consists of a pin which is rounded at the front and has an outer diameter which corresponds approximately to the inner diameter of the vessel. The pin is at least as long as the part of the vessel protruding beyond the sleeve, and has an axial bore which opens at its front end. Through this bore, a physiologically compatible pressurized fluid is pumped outwards during the turning-over operation.

The rear part of the auxiliary device is cylindrical, and its diameter is larger than that of the pin. The front side of this rear part facing towards the vessel is concave in advantageous embodiments.

When the front part of the pin enters the vessel, a pressure builds up in the vessel. Since the vessel is additionally clamped at the rear, the fluid pumped through the pin has to flow outwards between the inner side of the vessel and the pin; in this way, a lubricating film is formed. The friction between the vessel and the pin is therefore very low, and the pin can consequently be easily inserted into the vessel.

The build-up of pressure in the vessel means that the latter is pressed against the inner side of said sleeve and a static friction is produced. The static friction can additionally be increased by a suitable structure of the inner side of the sleeve, so that the vessel, despite the pressure in its interior, cannot expand backwards but rather adheres to the inner side of the sleeve.

Until the protruding end of the vessel has reached the front side of the rear part of the auxiliary device, nothing else happens. However, once the end of the vessel meets this front face, it is pushed back in the direction of the sleeve. However, that part of the vessel which is located in the interior of the sleeve cannot move back on account of the aforementioned static friction.

The part of the vessel protruding beyond the sleeve is therefore upset. At the same time, the pressure in the fluid increases. As a result, the protruding part of the vessel widens. Since the fluid has to flow between the end of the vessel and the front side of the rear part of the auxiliary device, there is also no static or sliding friction here which could hinder the widening of the vessel.

The upsetting and widening of the protruding part of the vessel has the result that the outer side of this vessel part starts to be placed around the end of the sleeve. As this process continues, an increasingly large part of the vessel is placed around the end of the sleeve. Ultimately the end of the vessel moves into an indifferent state of equilibrium, and from this point it is completely turned over into a stable position under a certain condition, without external intervention. The condition is that the protruding end of the vessel was originally not too long.

BRIEF DESCRIPTION OF THE DRAWINGS

A preferred example of embodiment of the invention will be described below with reference to the appended drawings, in which.

DETAILED DESCRIPTION OF THE INVENTION

Figure 1:
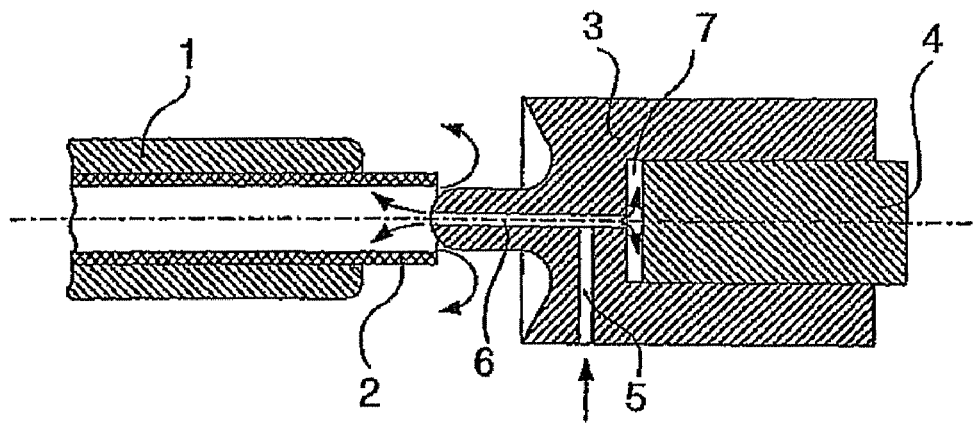
FIG. 1 shows a turning-over device in the state before the front part of the auxiliary device moving towards the vessel opening enters the vessel.

FIG. 1 shows the essential parts of a turning-over device which is suitable for the overall system on account of its compact design and simplicity: a sleeve (1) which is pushed over a vessel (2), a movable auxiliary device (3) and a piston (4) which protrudes into a cylindrical opening (7) of the rear part of the auxiliary device (3). All parts are axially aligned. The sleeve (1), the vessel (2) and the piston (4) are stationary parts, while the auxiliary device (3), on which the piston (4) is mounted, can be moved in the axial direction. The auxiliary device (3) has an opening (5) into which a physiologically compatible fluid is pressed. The fluid flows through an axial channel (6) both into the interior of the vessel (2) and into the cylinder chamber (7). The fluid pushes against the piston (4) and thus makes the auxiliary device (3) move in the direction of the vessel (2). Since it is a condition that the vessel (2) is clamped in or behind the sleeve (1), the fluid has to flow outwards between the vessel (2) and the front part of the auxiliary device (3). This ensures that the friction between the vessel (2) and the front part of the auxiliary device (3) is low and the front part of the auxiliary device (3) can easily enter the vessel (2).

Figure 2:
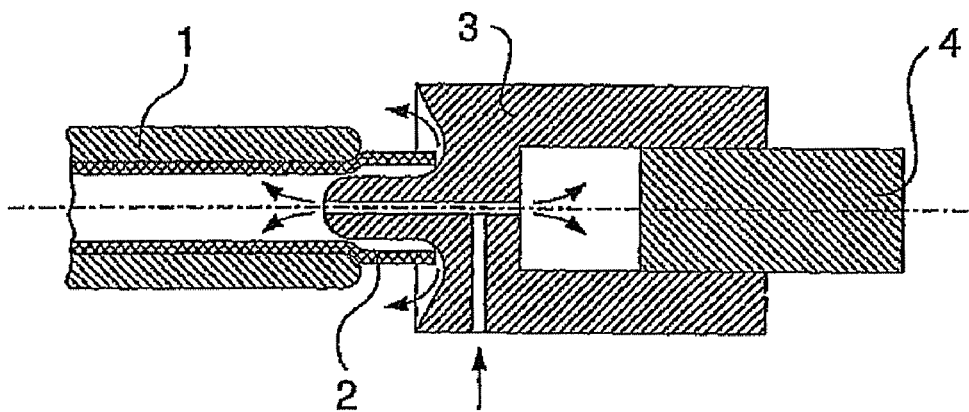
FIG. 2 shows the moment at which the end of the vessel butts against the rear part of the auxiliary device for the first time.

FIG. 2 shows the moment at which the end of the vessel (2) butts against the front side of the rear part of the auxiliary device (3). The pressure in the interior of the vessel (2) increases. As a result, the vessel (2) is pressed against the inner side of the sleeve (1) and the static friction increases. The vessel (2) therefore cannot slide back when the rear part of the auxiliary device (3) then starts to upset the end of the vessel (2). As a result of the pressure in the fluid and the upsetting, the end of the vessel (2) is widened and starts to nestle around the end of the sleeve (1).

Figure 3:
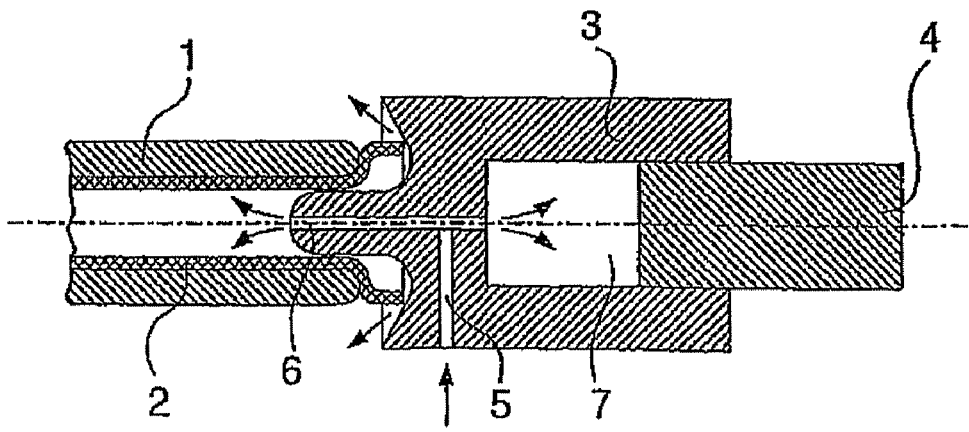
FIG. 3 shows the upset and widened end of the vessel.
Figure 4:
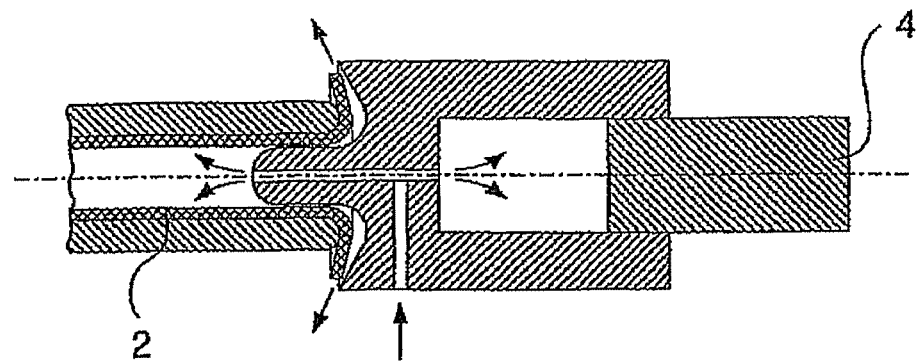
FIG. 4 shows the moment at which the end of the vessel reaches an indifferent state of equilibrium.

FIG. 3 shows the state at a subsequent point in time. The end of the vessel (2) has been upset further and has been further placed around the end of the sleeve (1). FIG. 4 shows the end of the vessel (2) in the indifferent state of equilibrium after even further upsetting and widening.

Figure 5:
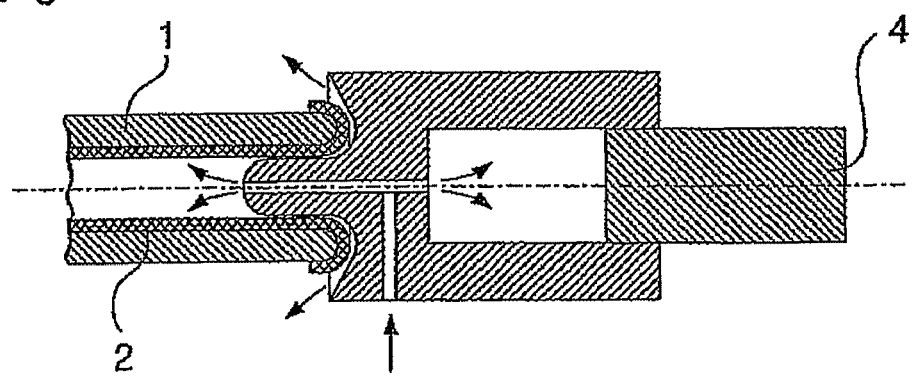
FIG. 5 shows a view of the completely turned-over vessel end at the end of the turning-over process.

Once the end of the vessel (2) has passed by itself into a new equilibrium position, it nestles fully around the end of the sleeve (1) as shown in FIG. 5.

Embodiments which operate without a piston (4) are also conceivable. In this case, however, the auxiliary device (3) should also be mounted such that it can be displaced in the axial direction, so as to allow easier insertion of the auxiliary device (3) into the vessel (2). The axial forward movement is then brought about for example manually or by spring force.

Figure 6:
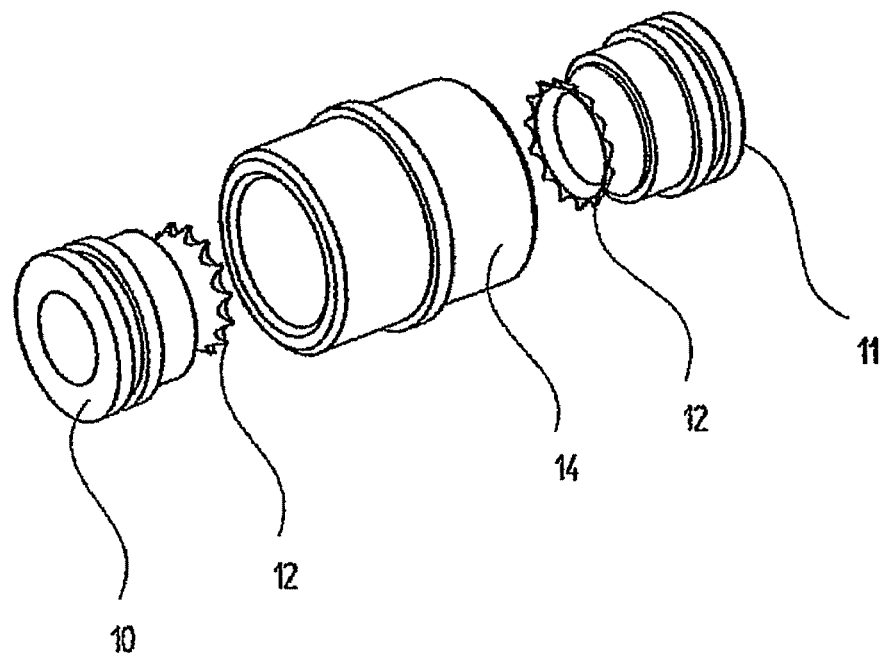
FIG. 6 shows a system which consists of three fittings for connecting two vessel ends.

FIG. 6 shows three fittings suitable for the end-to-end anastomosis of hollow organs. The connection is established as follows: one end of each of the hollow organs to be connected is pushed into a respective sleeve (10, 11), namely until the hollow organs protrude slightly beyond the ends (12) of the sleeves. The ends of the hollow organs are then turned over around the ends (12) of the sleeves. The sleeves (10, 11) are then pushed into the third sleeve (14) until the turned-over parts of the hollow organs make contact with one another. The two sleeves (10, 11) are then fixed in this position.

The fittings (10) and (11) are of identical design. Their inner diameter corresponds approximately to the outer diameter of the hollow organs to be connected. The ends (12) of the sleeves are shaped in such a way that the outer diameter of the turned-over hollow organs is the same as or smaller than the inner diameter of the sleeve (14). Furthermore, the ends (12) of the sleeves may have spikes, prongs or barbs so that the turned-over hollow organs can no longer become detached.

In order for the connection to be established, further conditions must be met: the fit between the inner diameter of the sleeve (14) and the outer diameter of the sleeves (10, 11) may be either a press/interference/push fit or a sliding fit. In the first case, the press/interference/push fit must be such that, after the sleeves (10, 11) have been pushed into the sleeve (14), they are secured in such a way that they cannot become detached under the expected tensile stress of the hollow organs.

In the second case, special fixing elements must be provided. For example, the sleeve (14) may have two annular grooves on its inner side, and the sleeves (10, 11) may each have a corresponding bead. The distance between the two grooves is selected in such a way that the inner sides of the turned-over hollow organs just make contact with one another when the beads of the sleeves (10, 11) are latched into the grooves of the sleeve (14). In order for the sleeves (10, 11) to be able to be pushed and latched by their beads into the sleeve (14), the latter must be stretchable in the radial direction.

It is also advantageous if the sleeve (14) is split in the centre and the two parts are connected by a spring acting in the axial direction, or if the central part of the sleeve (14) is designed as such a spring. The spring constant is selected in such a way that, after the sleeves (10, 11) have been pressed or latched into the sleeve (14), the two turned-over hollow organ end pieces are pressed together with a defined force.

The fittings are advantageously made from biodegradable material, and the inner sides of the fittings (10, 11) advantageously have a surface texture; this increases the static friction between the fitting and the hollow organ during the turning-over process described above.

Figure 7:
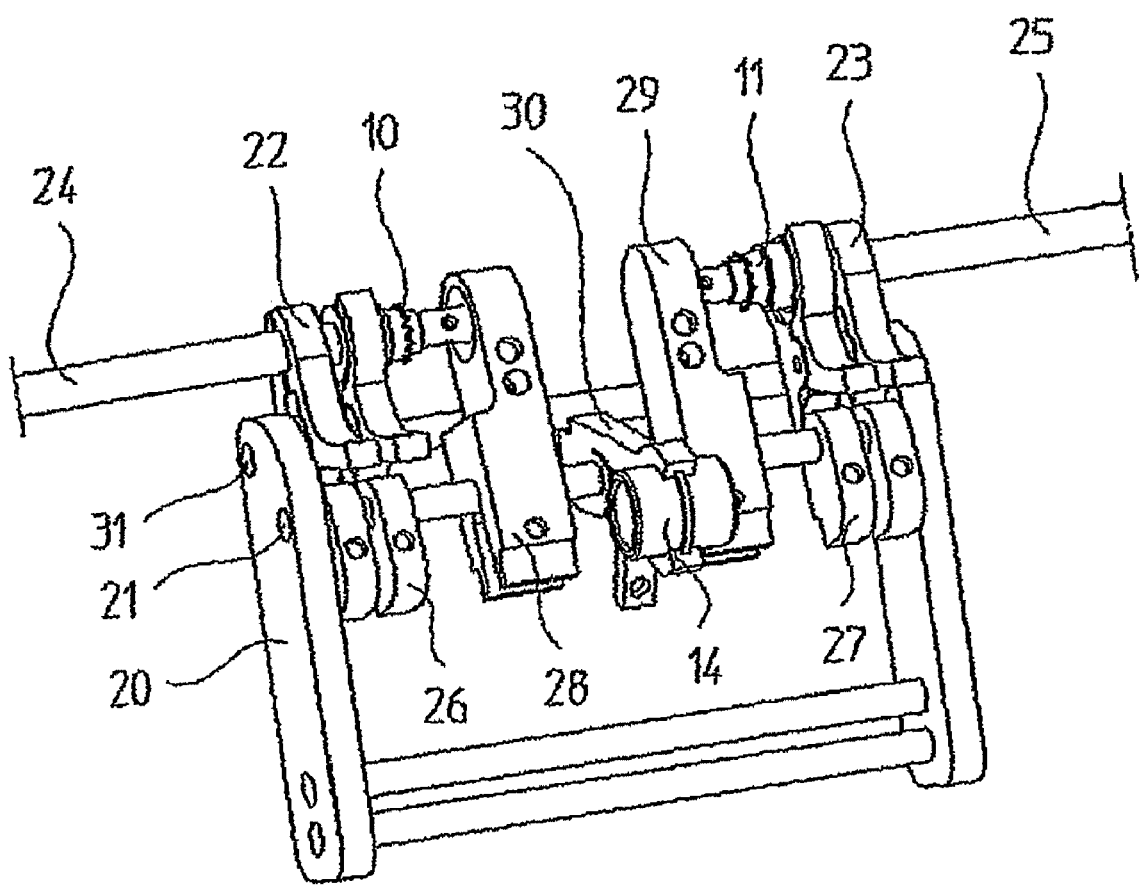
FIG. 7 shows a complete device with holding devices for vein clamps, holding devices for fittings or sleeves, a space-saving auxiliary device for turning over the ends of the blood vessels, and a rail system on which the holding devices can be laterally displaced, rotated, fixed in position and in some cases pushed on and removed.

FIG. 7 shows a complete system for the end-to-end anastomosis of hollow organs. A rigid frame (20) forms the basis of the system. Various holding devices are mounted in a rotatable and displaceable manner on a shaft (21). In order for said holding devices to be able to be aligned axially with one another, the crossbar (31) is designed as a stop. When the holding devices are rotated backwards as far as this stop, they are axially aligned.

A respective clamping device (22, 23) is mounted on the far right and far left. These serve to clamp and simultaneously secure the two hollow organs (24, 25) to be connected. Directly next to each clamping device, there is a respective device (26, 27) for securing the fittings (10, 11). A turning-over device (28) is located to the right next to the holding device (26) for the fitting (10), and a turning-over device (29) is located to the left next to the holding device (27) for the fitting (11). These turning-over devices can be pushed onto the shaft (21). After the hollow organs have been turned over, they are no longer required and can be removed.

Located in the centre of the system is a further holding device (30) for the third fitting (14). This displaceable holding device, after being rotated as far as the stop (31), is firstly pushed towards the holding device (26). In the process, the fitting (14) is pushed over the fitting (10) and the two parts are fixed relative to one another. The hollow organ (24) with the fitting (10) is then removed from the holding devices (22) and (26) and is pushed together with the holding device (30) towards the holding device (27). In the process, the fitting (14) is pushed over the fitting (11) and the two parts are fixed relative to one another. After the connection at both sides, the end-to-end connection is established and the hollow organs that have been coupled together can be removed together with their fittings (10, 11, 14) from the holding devices (23, 27, 30).

The invention claimed is:

1. A device for the anastomosis of hollow organs, comprising:
   two fittings or sleeves which can be pushed over two ends of hollow organs to be connected in such a way that said two ends protrude beyond ends of said two fittings or sleeves by a defined extent,
   one or more turning-over devices configured for turning over the ends of the hollow organs around the ends of said fittings or sleeves, a third fitting into which the two fittings or sleeves with the turned-over hollow organ ends can be pushed and fixed in such a way that the inner sides of the hollow organ ends make contact with one another, a system of holding devices which are mounted on one or more rails and have one or more of the following properties: can be displaced laterally, can be removed, can be pushed on, can be rotated, can be fixed in position, wherein these holding devices can accommodate said two fittings or sleeves, can hold said turning-over devices, can in any case hold clamps for holding and clamping the hollow organs, and can be axially aligned with one another by means of a further auxiliary device.

2. The device according to claim 1, wherein the turning-over device is a rotationally symmetrical auxiliary device, a front part of which consists of a pin having a diameter which corresponds approximately to the inner diameter of one of said hollow organs, and a rear part of which has a diameter which is larger than that of the front part, and in that, during the turning-over process, a pressurized fluid is pressed out of said pin via an outlet or via a number of outlets, and for turning-over purposes, the turning over device is configured to push with the front part into the opening of the hollow organ clamped in or behind one of said two fittings or sleeves until the end of the hollow organ has been placed around the end of said fitting or sleeve.

3. The device according to claim 2, wherein a front side of the rear part of said rotationally symmetrical auxiliary device has a concave part configured to face the opening of the hollow organ.

4. The device according to claim 2, wherein the rear part of said rotationally symmetrical auxiliary device contains for drive purposes, a cylinder and a piston, which is supplied from the same fluid source as the outlets of said rotationally symmetrical auxiliary device.

5. The device according to claim 1, wherein the fit of said two fittings or sleeves for accommodating the hollow organ ends and of the third fitting for accommodating said two fittings or sleeves allows a press fit, an interference fit or a push fit.

6. The device according to claim 5, wherein said third fitting for accommodating the two other said fittings or sleeves comprises parts that are connected via an axially flexible central part so that, after the latching-in of the two other said fittings or sleeves, a defined force is exerted on the turned-over hollow organ ends.

7. The device according to claim 1, wherein each of said two fittings or sleeves for accommodating the hollow organ ends has at least one groove or one bead running around the entire outer circumference, and in that said third fitting for accommodating the two other said fittings or sleeves has at least two beads or grooves running around the entire inner circumference, into which the grooves or the beads of the two other said fittings or sleeves can latch.

8. The device according to claim 7, wherein the third fitting for accommodating the two other said fittings or sleeves is completely or partially slit in the longitudinal direction in order to allow or to facilitate the insertion of the two other said fittings or sleeves.

9. The device according to claim 1, wherein the inner side of said fittings or sleeves for accommodating the hollow organ ends have a surface structure which increases the static friction when the hollow organ is pressed against the inner side, but which at the same time does not substantially hinder the insertion of the hollow organ into the fitting or sleeve.

10. The device according to claim 7, wherein said third fitting for accommodating the two other said fittings or sleeves comprises parts that are connected via an axially flexible central part so that, after the latching-in of the two other said fittings or sleeves, a defined force is exerted on the turned-over hollow organ ends.

* * * * *

UNITED STATES PATENT AND TRADEMARK OFFICE
CERTIFICATE OF CORRECTION

| | | |
|---|---|---|
| PATENT NO. | : 7,955,342 B2 | Page 1 of 1 |
| APPLICATION NO. | : 11/997387 | |
| DATED | : June 7, 2011 | |
| INVENTOR(S) | : Falah Redha et al. | |

It is certified that error appears in the above-identified patent and that said Letters Patent is hereby corrected as shown below:

Title Page, Item (75) Inventors: "Falah Redha, Riyadh (SA)" should read --Falah Redha, Bern (CH)--.

Signed and Sealed this
Twenty-third Day of August, 2011

David J. Kappos
*Director of the United States Patent and Trademark Office*